US008808298B2

(12) United States Patent
Raub et al.

(10) Patent No.: US 8,808,298 B2
(45) Date of Patent: Aug. 19, 2014

(54) PIVOTING CUT GUIDES

(75) Inventors: Kevin M. Raub, Warsaw, IN (US);
Vijay N. Permeswaran, Le Mars, IA (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/475,545

(22) Filed: May 18, 2012

(65) Prior Publication Data
US 2013/0310836 A1    Nov. 21, 2013

(51) Int. Cl.
*A61B 17/15* (2006.01)
(52) U.S. Cl.
USPC .......................................... 606/88
(58) Field of Classification Search
USPC ........... 606/79, 82, 86 R, 87, 88, 89, 90, 102, 606/105
See application file for complete search history.

(56) References Cited

U.S. PATENT DOCUMENTS

| | | | |
|---|---|---|---|
| 5,611,802 A | | 3/1997 | Samuelson et al. |
| 5,735,856 A * | | 4/1998 | McCue et al. .................. 606/87 |
| 5,916,221 A * | | 6/1999 | Hodorek et al. ................ 606/89 |
| 7,318,827 B2 | | 1/2008 | Leitner et al. |
| 7,364,581 B2 | | 4/2008 | Michawlowicz |
| 7,621,920 B2 | | 11/2009 | Claypool et al. |
| 8,313,491 B2 * | | 11/2012 | Green et al. .................... 606/88 |
| 2006/0122617 A1 * | | 6/2006 | Lavallee et al. ................ 606/87 |
| 2007/0213738 A1 * | | 9/2007 | Martin et al. .................. 606/87 |
| 2008/0015604 A1 | | 1/2008 | Collazo |
| 2008/0039850 A1 | | 2/2008 | Rowley et al. |
| 2008/0172054 A1 | | 7/2008 | Claypool et al. |
| 2009/0087276 A1 | | 4/2009 | Rose |
| 2009/0088753 A1 | | 4/2009 | Aram et al. |
| 2009/0088754 A1 | | 4/2009 | Aker et al. |
| 2009/0088755 A1 | | 4/2009 | Aker et al. |
| 2009/0088758 A1 | | 4/2009 | Bennett |
| 2009/0088759 A1 | | 4/2009 | Aram et al. |
| 2009/0088760 A1 | | 4/2009 | Aram et al. |
| 2009/0088761 A1 | | 4/2009 | Roose et al. |
| 2009/0088763 A1 | | 4/2009 | Aram et al. |

(Continued)

FOREIGN PATENT DOCUMENTS

WO    WO2008/005271 A2    1/2008

OTHER PUBLICATIONS

"Zimmer NexGen LCCK Surgical Technique for use with LCCK 4-in-1 Instrumentation", Zimmer, Inc.; copyright 2009, 2010, 2011, (May 2011), 52 pgs.

*Primary Examiner* — Michael T Schaper
*Assistant Examiner* — Amy Sipp
(74) *Attorney, Agent, or Firm* — Schwegman Lundberg & Woessner, P.A.

(57) ABSTRACT

The present disclosure provides a cut guide for use in preparation of the distal femur to form the anterior, anterior chamfer, distal, posterior chamfer and posterior facets as well as the intercondylar box cuts utilized to prepare a femoral intercondylar box. To allow for the use of a single cutting guide to make all of these femoral osteotomies, the present disclosure implements an orthopedic guide assembly including a primary guide body with a secondary guide body rotatably connected to the primary guide body. With this configuration, the secondary guide body can be rotated into an operable position to guide a femoral osteotomy and may also be rotated into an inoperable position in which it is moved from a configuration (i.e., the operable position) in which it acts as a barrier to movement of an osteotome across a guide surface of the primary guide body.

16 Claims, 5 Drawing Sheets

(56) References Cited

U.S. PATENT DOCUMENTS

| | | |
|---|---|---|
| 2009/0093816 A1 | 4/2009 | Roose et al. |
| 2009/0099567 A1 | 4/2009 | Zajac |
| 2009/0131942 A1 | 5/2009 | Aker et al. |
| 2010/0191244 A1 | 7/2010 | White et al. |
| 2010/0305711 A1 | 12/2010 | McKinnon et al. |
| 2011/0046629 A1 | 2/2011 | Green, II et al. |
| 2011/0213378 A1* | 9/2011 | Dees, Jr. .................. 606/89 |
| 2011/0218541 A1* | 9/2011 | Bailey et al. ............. 606/88 |
| 2011/0307067 A1* | 12/2011 | Dees ...................... 623/20.35 |
| 2012/0310246 A1* | 12/2012 | Belcher et al. ............ 606/80 |
| 2013/0310836 A1* | 11/2013 | Raub et al. ............... 606/84 |
| 2013/0325016 A1* | 12/2013 | Sordelet et al. .......... 606/87 |
| 2013/0325021 A1* | 12/2013 | Sordelet et al. .......... 606/89 |

* cited by examiner

PIVOTING CUT GUIDES

BACKGROUND

1. Technical Field

The present disclosure relates to cut guides for guiding the resection of a bone to receive a prosthesis component. More particularly, the present disclosure relates to a cut guide for guiding osteotomy of the distal femur to receive a femoral prosthesis having an intercondylar box, e.g., a posterior stabilized femoral prosthesis.

2. Description of the Related Art

Orthopedic prostheses are commonly utilized to repair and/or replace damaged bone and tissue in the human body. For example, a knee prosthesis may include a femoral component which replaces the articular surface of one or both of the natural femoral condyles. Often, the femoral component articulates with a tibial component secured to the proximal end of the patient's tibia so that the knee prosthesis completely replaces the articular surfaces of the natural femur and tibia. A tibial bearing component, which may also be referred to as a tibial insert or a meniscal component is positioned between the femoral prosthesis and the tibia and provides an articular surface which interacts with the femoral component during extension and flexion of the knee.

To prepare the femur and tibia to receive the femoral prosthesis and the tibial prosthesis, respectively, bone cuts or "osteotomies" must be performed to reshape the bones of a joint to receive the prosthetic components. Typically, a single tibial osteotomy is made transverse to the anatomic axis of the tibia. To prepare the femur to receive a femoral prosthesis, five femoral "box cuts" are typically made. The box cuts include osteotomies to form an anterior facet, an anterior chamfer facet, a distal facet, a posterior chamfer facet and a posterior facet on the femur.

Bone cutting instruments are generally referred to as osteotomes and include instruments such as articulating saws, for example, reciprocating or oscillating saws. Cut guides having guide surfaces sized and shaped to guide osteotomes are implemented to facilitate proper location and sizing of bone osteotomies to allow for implantation of prosthesis components.

Femoral prosthesis designs include posterior stabilized prostheses including a spine protruding proximally from the meniscal component and a cam positioned in the intercondylar fossa of the femoral prosthesis component. In posterior stabilized designs, the femoral cam interacts with the tibial spine during flexion of the knee. Posterior stabilized prostheses are typically used in surgical situations in which the posterior cruciate ligament is absent. Posterior stabilized configurations can have varying levels of constraint. An example of a highly constrained design is the Zimmer® NexGen® LCCK which is described together with the surgical technique for implanting the same in the Zimmer® NexGen® LCCK Surgical Technique for Use with LCCK 4-in-1 Instrumentation bearing copyright dates of 2009, 2010 and 2011, the entire disclosure of which is hereby explicitly incorporated by reference herein, a copy of which is included with an Information Disclosure Statement filed in the present application.

To allow for implantation of a posterior stabilized knee prosthesis, intercondylar box cuts must be made in addition to the five femoral "box cuts" described above. Intercondylar box cuts are made from the distal end of the femur toward the proximal end of the femur to remove a portion of the intercondylar fossa which will be replaced by the intercondylar box of the femoral prosthesis so that the intercondylar box of the femoral prosthesis can interact with the tibial spine.

SUMMARY

The present disclosure provides a cut guide for use in preparation of the distal femur to form the anterior, anterior chamfer, distal, posterior chamfer and posterior facets as well as the intercondylar box cuts utilized to prepare a femoral intercondylar box sized to receive a femoral prosthesis intercondylar box. To allow for the use of a single cutting guide to make all of these femoral osteotomies, the present disclosure implements an orthopedic guide assembly including a primary guide body with a secondary guide body rotatably connected to the primary guide body. With this configuration, the secondary guide body can be rotated into an operable position to guide a femoral osteotomy across a first guide surface of the secondary guide body. The secondary guide body may also be rotated into an inoperable position in which it is moved away from a configuration (i.e., the operable position) in which it acts as a barrier to movement of an osteotome across a guide surface of the primary guide body.

The invention, in one form thereof, comprises an orthopedic guide assembly including a primary guide body having a bone contacting surface in a primary guide body opposing surface opposite the bone contacting surface, the primary guide body defining a first primary guide surface extending between the bone contacting surface and the primary guide body opposing surface, the first primary guide surface sized and shaped to guide a primary osteotome to prepare a first primary osteotomy of a bone, the first primary guide surface having a first primary guide surface extent over which the primary osteotome can be guided to prepare a full extent of the primary osteotomy of the bone; and a secondary guide body having a bone side surface and a secondary guide body opposing surface opposite the bone side surface, the secondary guide body defining a secondary guide surface extending between the bone side surface and the secondary guide body opposing surface, the secondary guide surface sized and shaped to guide a selected one of the primary osteotome and a secondary osteotome to prepare a secondary osteotomy of the bone, the secondary guide body rotatably connected to the primary guide body, the secondary guide body rotatable from an operative position in which the secondary guide body is operably positioned to guide preparation of the secondary osteotomy to a non-operative position in which the secondary guide is not capable of guiding preparation of the secondary osteotomy, in the operative position the secondary guide body presents a barrier to movement of the primary osteotome guided by the first primary guide surface so that movement of the primary osteotome is restricted to less than movement over a full extent of the first primary guide surface extent when the secondary guide body maintains the operative position, in the non-operative position the secondary guide body does not present the barrier to movement of the primary osteotome guided by the first primary guide surface to less than movement over the full extent of the first primary guide surface extent, the first primary guide surface extent fully accessible by the primary osteotome to prepare the full extent of the primary osteotomy of the bone when the secondary guide body maintains the non-operative position and the first primary guide surface extent is not fully accessible by the primary osteotome to prepare the full extent of the primary osteotomy of the bone when the secondary guide body maintains the operative position.

The invention, in another form thereof, comprises an orthopedic instrument set including a primary osteotome, including a primary osteotome blade, a primary osteotome handle extending from the primary osteotome blade. The orthopedic instrument set of this form of the present invention further includes a primary guide body having a bone contacting surface and a primary guide body opposing surface opposite the bone contacting surface, the primary guide body defining a first primary guide surface extending between the bone contacting surface and the primary guide body opposing surface, the first primary guide surface sized and shaped to guide the primary osteotome blade to prepare a first primary osteotomy of a bone, the first primary guide surface having a first primary guide surface extent over which the primary osteotome blade can be guided to prepare a full extent of the primary osteotomy of the bone. The orthopedic instrument set of this form of the present invention further includes a secondary osteotome including a secondary osteotome blade and a secondary osteotome handle extending from the secondary osteotome blade. Further, the orthopedic instrument set of this form of the present invention includes a secondary guide body having a bone side surface and a secondary guide body opposing surface opposite the bone side surface, the secondary guide body defining a secondary guide surface extending between the bone side surface and the secondary guide body opposing surface, the secondary guide surface sized and shaped to guide a selected one of the primary osteotome and the secondary ostetome to prepare a secondary osteotomy of the bone, the secondary guide body rotatably connected to the primary guide body, the secondary guide body rotatable from an operative position in which the secondary guide is operably positioned to guide preparation of the secondary osteotomy to a non-operative position in which the secondary guide is not capable of guiding preparation of the secondary osteotomy, in the operative position the secondary guide body present a barrier to movement of the primary osteotome blade guided by the first primary guide surface so that movement of the primary osteotome is restricted to less than movement over a full extent of the first primary guide surface extent when the secondary guide body maintains the operative position, in the non-operative position the secondary guide body does not present the barrier to movement of the primary osteotome blade guided by the first primary guide surface to less than movement over the full extent of the first primary guide surface extent, the first primary guide surface extent fully accessible by the primary ostetome to prepare the full extent of the primary osteotomy of the bone when the secondary guide body maintains the non-operative position and the first primary guide surface extent is not accessible by the primary ostetome to prepare the full extent of the primary osteotomy of the bone when the secondary guide body maintains the operative position.

The invention in a further form thereof, comprises a method of preparing a femur to receive a posterior stabilized femoral prosthesis, the posterior stabilized femoral prosthesis having a femoral prosthesis intercondylar box sized to receive a spine extending proximally from a tibial prosthesis, the method comprising the steps of: providing an orthopedic guide assembly including a primary guide body having a bone contacting surface and an opposing surface opposite the bone contacting surface, the primary guide body defining a first primary guide surface extending between the bone contacting surface and the opposing surface and a secondary guide body defining a secondary guide surface extending between the bone contacting surface and the opposing surface, the secondary guide body rotatably connected to the primary guide body; positioning the bone contacting surface of the primary guide body in contact with the femur; securing the orthopedic guide assembly relative to the femur; rotating the secondary guide body to a non-operative position and thereby allowing movement of a primary osteotome over a full extent of the first primary guide surface; after the step of rotating the secondary guide body to the non-operative position, guiding the primary osteotome with the first primary guide surface to make a first intercondylar box cut in the femur to prepare a femoral intercondylar box sized to receive the femoral prosthesis intercondylar box; rotating the secondary guide body to an operative position; and after the step of rotating the secondary guide body to an operative position, preparing an anterior facet on the femur using the secondary guide surface to guide the step of preparing the anterior facet of the femur, the anterior facet intersecting the first intercondylar box cut.

BRIEF DESCRIPTION OF THE DRAWINGS

The above mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

Figure 1:
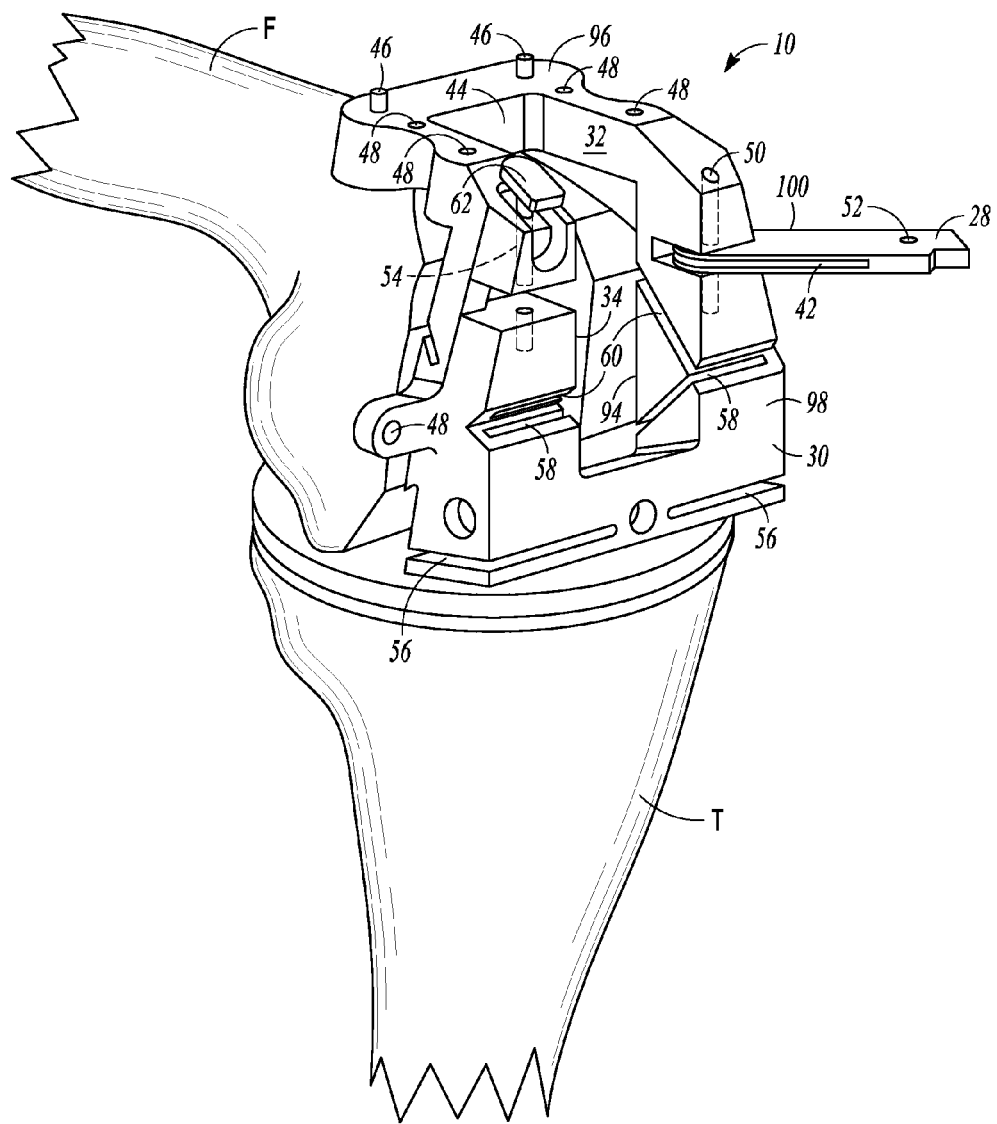
FIG. 1 is a perspective view of a knee joint with an orthopedic guide assembly of the present disclosure secured thereto and illustrating a secondary guide body rotated to a non-operative position in which the secondary guide is not capable of guiding preparation of an osteotomy of the femur.
Figure 5:
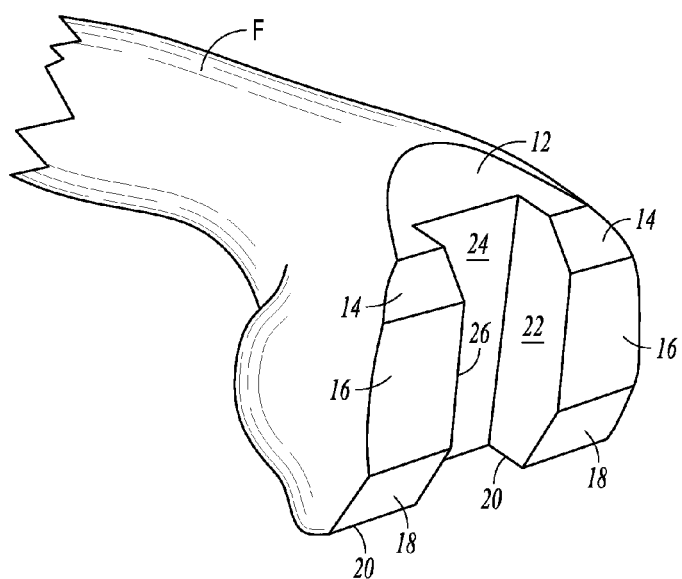
FIG. 5 is a perspective view of a femur illustrating the five femoral box cuts as well as intercondylar box cuts.

Referring to FIGS. 1 and 5, orthopedic guide assembly 10 (FIG. 1) includes a number of guide surfaces extending from bone contacting surface 94 to opposing surface 98 and configured for guiding osteotomes to prepare anterior facet 12, anterior chamfer facet 14, distal facet 16, posterior chamfer facet 18, posterior facet 20 and intercondylar box facets 22, 24 and 26 (FIG. 5). In an exemplary embodiment, intercondylar box facet 22 is parallel to intercondylar box facet 26, and intercondylar box facet 24 is orthogonal to intercondylar box facets 22 and 26. FIG. 1 illustrates secondary guide body 28 rotated relative to primary guide body 30 to a non-operative position in which secondary guide body 28 is not capable of guiding preparation of one of the femoral osteotomies depicted in FIG. 5 and in which secondary guide body 28 does not present a barrier to movement of an osteotome guided by first primary guide surface 32 or second primary guide surface 34. In this position of secondary guide body 28, first primary guide surface 32 and second primary guide surface 34 may be utilized to guide preparation of intercondylar box facets 22, 26.

As illustrated in FIG. 1, bone contacting surface 94 extends from a distal bone contacting surface to an anterior bone contacting surface positioned generally orthogonal to the distal bone contacting surface. In an alternative embodiment, orthopedic guide assembly 10 will be formed of two detachable components such that the portion of orthopedic guide assembly 10 in which the anterior bone contacting surface portion of bone contacting surface 94 is formed, will be removeable from the remainder of orthopedic guide assembly 10. This will allow secondary guide body 28 to be utilized to form anterior facet 12 as will be further described hereinbelow prior to connection of the two pieces of orthopedic guide assembly 10 such that the portion of orthopedic guide assembly 10 which includes the anterior bone contacting portion of bone contacting surface 94 can rest on prepared anterior facet 12.

Because bone contacting surface 94 extends from a distal bone contacting surface to an anterior bone contacting surface, both an anterior to posterior and a distal to proximal approach may be taken for the preparation of intercondylar box facets 22, 26 (FIG. 5). In a further alternative embodiment, the portion of orthopedic guide assembly 10 which includes the anterior bone contacting surface portion of bone contacting surface 94 can be completely excluded from the device. In this embodiment, a primarily distal to proximal approach will be taken for the preparation of intercondylar box facets 22, 26 (FIG. 5). Throughout this document, directional terms such as anterior, posterior, proximal, distal, medial and lateral are used in their anatomic sense. For example, anterior denotes a position toward the front of the body, while posterior denotes a position toward the rear of the body, proximal denotes a position near to the trunk of the body while distal denotes a position further from the trunk of the body, and medial denotes a position nearer to the middle or midsagittal plane of the body while distal denotes a position further from the middle or midsagittal plane of the body. With reference to instruments and implants of the present disclosure, these terms are utilized in reference to the operative position of the instrument or implant relative to the relevant anatomic structure.

Figure 2:
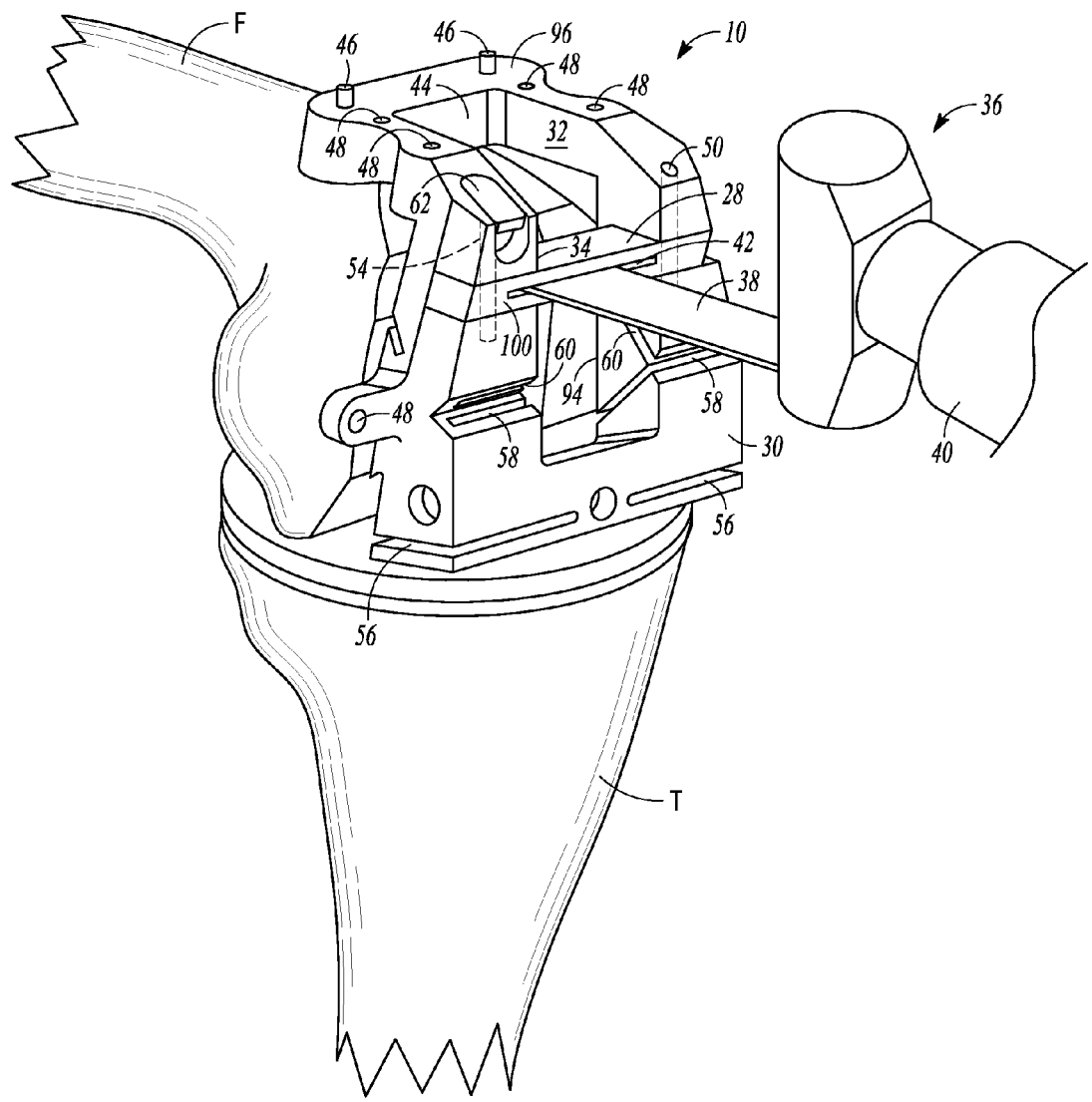
FIG. 2 illustrates the knee/orthopedic guide assembly of FIG. 1, with the secondary guide body rotated from the non-operative position illustrated in FIG. 1 to an operative position in which the secondary guide is operably positioned to guide preparation of an osteotomy.

Secondary guide body 28 includes cut slot 42 extending from bone side surface 98 to opposing surface 100 of secondary guide body 28. FIG. 2 illustrates secondary guide body 28 rotated from the non-operative position illustrated in FIG. 1 to an operative position in which secondary guide body 28 is operably positioned to guide preparation of an osteotomy to form anterior facet 12 (FIG. 5). As illustrated in FIG. 2, the operative position of secondary guide body 28 places secondary guide body 28 in a position where it spans first primary guide surface 32 and second primary guide surface 34 and presents a barrier to movement of an osteotome guided by first primary guide surface 32 or second primary guide surface 34.

Oscillating saw 36 depicted in FIG. 2 is an exemplary osteotome that can be utilized to osteotomize femur F. Alternative osteotomes include reciprocating saws, bone chisels. As illustrated in FIG. 2, oscillating saw 36 includes blade 38. Extending from blade 38 is handle 40. As illustrated in FIG. 2, blade 38 of oscillating saw 36 is guided by secondary guide body 28 when blade 38 is introduced into cut slot 42 of secondary guide body 28. In this configuration, either the upper or lower walls forming cut slot 42 can be positioned such that the upper and/or lower surface of blade 38 is flush therewith so that the trajectory of blade 38 is defined by either the upper or the lower surface forming cut slot 42, or by both the upper and lower surfaces. In the operative position illustrated in FIG. 2, a guide plane defined by first primary guide surface 32 forms an angle with a guide plane defined by the guide surfaces of cut slot 42. This angle is maintained when secondary guide body 28 is moved to the non-operative position illustrated in FIG. 1. In one exemplary embodiment, these guide planes are orthogonal to each other such that anterior facet 12 will be orthogonal to box facets 22, 26 when the resection of femur F is complete.

When forming intercondylar box facets 22, 24 and 26, an osteotome will have its blade positioned flush with primary guide surface 32, second primary guide surface 34, and tertiary guide surface 44. First primary guide surface 32, second primary guide surface 34 and tertiary guide surface 44 are sized and shaped to guide the preparation of intercondylar box facets 22, 26 and 24, respectively. In one exemplary embodiment, first primary guide surface 32 is orthogonal to second primary guide surface and second primary guide surface 34 is orthogonal to tertiary guide surface 44. In this configuration, first primary guide surface 32 faces second primary guide surface 34.

Before utilizing the various guide surfaces of orthopedic guide assembly 10, pins 46 may be passed through pin apertures 48 to secure orthopedic guide assembly 10 to femur F. While only two pins 46 are depicted in FIGS. 1 and 2 of the present application, any number of pins and associated pin apertures 48 may be utilized to secure orthopedic guide assembly 10 to femur F.

Referring to FIGS. 1 and 2, secondary guide body 28 is rotatably connected via pivot pin 50 to primary guide body 30. Further, secondary guide body 28 includes aperture 52 (FIG. 1) through which fixation pin 54 can be positioned to secure secondary guide body 28 in the operable position illustrated in FIG. 2. Button 62 is fixed to fixation pin 54 and may be utilized to raise or lower fixation pin 54 out of or into engagement with aperture 52. In an alternative embodiment, fixed pivot pin 50 is replaced with a second articulating fixation pin 54. In this embodiment, either fixation pin 54 may be articulated out of engagement with the corresponding aperture 52 in secondary guide body 28 to allow for rotation of secondary guide body 28 about the opposite fixation pin 54. In this embodiment, with one fixation pin 54 engaging a corresponding aperture 52 in secondary guide body 28 and the other fixation pin disengaged from secondary guide body 28, the engaged pin 54 will serve as a pivot rotably connecting secondary guide body 28 to primary guide body 30.

In addition to the previously mentioned guide surfaces, primary guide body 30 further includes posterior guide slots 56, posterior chamfer guide slots 58 and anterior chamfer guide slots 60. Posterior guide slots 56, posterior chamfer guide slots 58 and anterior chamfer guide slots 60 include upper and lower surfaces which may be utilized to guide an osteotome, such as oscillating saw blade 38, to create facets 20, 18 and 14, respectively, in similar fashion as described above with reference to cut slot 42. In one exemplary embodiment, the guide planes established by the guide surfaces of posterior guide slots 56 form an angle of about 45° with the guide planes established by the guide surfaces of posterior chamfer guide slots 58. Further, the guide plane established by the guide surfaces of posterior chamfer guide slots 58 forms an angle of about 45° with the distal portion of bone contacting surface 94 which is positioned atop distal facet 16 (FIG. 5) in use. Additionally, the guide plane formed by the guide surfaces of anterior chamfer guide slots 60 forms an angle of about 45° relative to the distal portion of bone contacting surface 94 which is positioned atop distal facet 16 (FIG. 5) in use. Further, guide planes established by the guide surfaces of anterior chamfer guide slots 60 form an angle of about 45° with respect to guide planes formed by the guide surfaces of cut slot 42 of secondary guide body 28. In certain exemplary embodiments, anterior facet 12 and posterior facet 20 will diverge from each other proximally. In these embodiments, the guide planes established by the guide surface of anterior chamfer guide slots 60 will form an angle of more than 45° with respect to the guide planes formed by the guide surfaces of cut slot 42 of secondary guide body 28. Similarly, in such an embodiment, the guide planes established by the guide surfaces of posterior chamfer guide slots 58 will form an angle of more than 45° with respect to the guide planes formed by the guide surfaces of posterior chamfer guide slots 58.

A posterior guide surface plane defined by the guide surfaces of posterior guide slots 56 intersects a posterior chamfer guide surface plane formed by posterior chamfer guide slots 58. The posterior guide surface plane further intersects an anterior chamfer guide surface plane defined by anterior chamfer guide slots 60. The posterior chamfer guide surface plane further intersects the anterior chamfer guide surface plane such that the facets illustrated in FIG. 5 can be formed. The guide surfaces of the orthopedic guide assembly of the present disclosure are all formed nominally as planar surfaces to facilitate guiding of the planar osteotomies depicted in FIG. 5. It will be appreciated by a person having ordinary skill in the art that "planar" when used in reference to a guide surface does not designate a perfectly geometrically planar surface but rather designates a surface which is nominally designed to be planar but which may deviate slightly from being perfectly geometrically planar due, e.g., to manufacturing tolerances. Prior to securement of orthopedic guide assembly 10 to femur F, distal facet 16 (FIG. 5) may be formed on femur F using a variety of well known instrumentation. After forming distal facet 16, a surgeon provides orthopedic guide assembly 10 to the patient and secures orthopedic guide assembly 10 to the patient within the medial lateral extent of the diaphysis of femur F. Bone contacting surface 94 of orthopedic guide assembly is planar so that it can be positioned flush with distal facet 16. With bone contacting surface 94 positioned flush with distal facet 16, anterior extension 96 can be positioned atop the anterior cortex of femur F and positioned thereon such that first primary guide surface 32, second primary guide surface 34 and tertiary guide surface 44 are aligned to guide formation of intercondylar box facets 22, 26 and 24, respectively. A surgeon may then provide one or more osteotomes to the patient to form the various osteotomies described herein.

Figure 3:
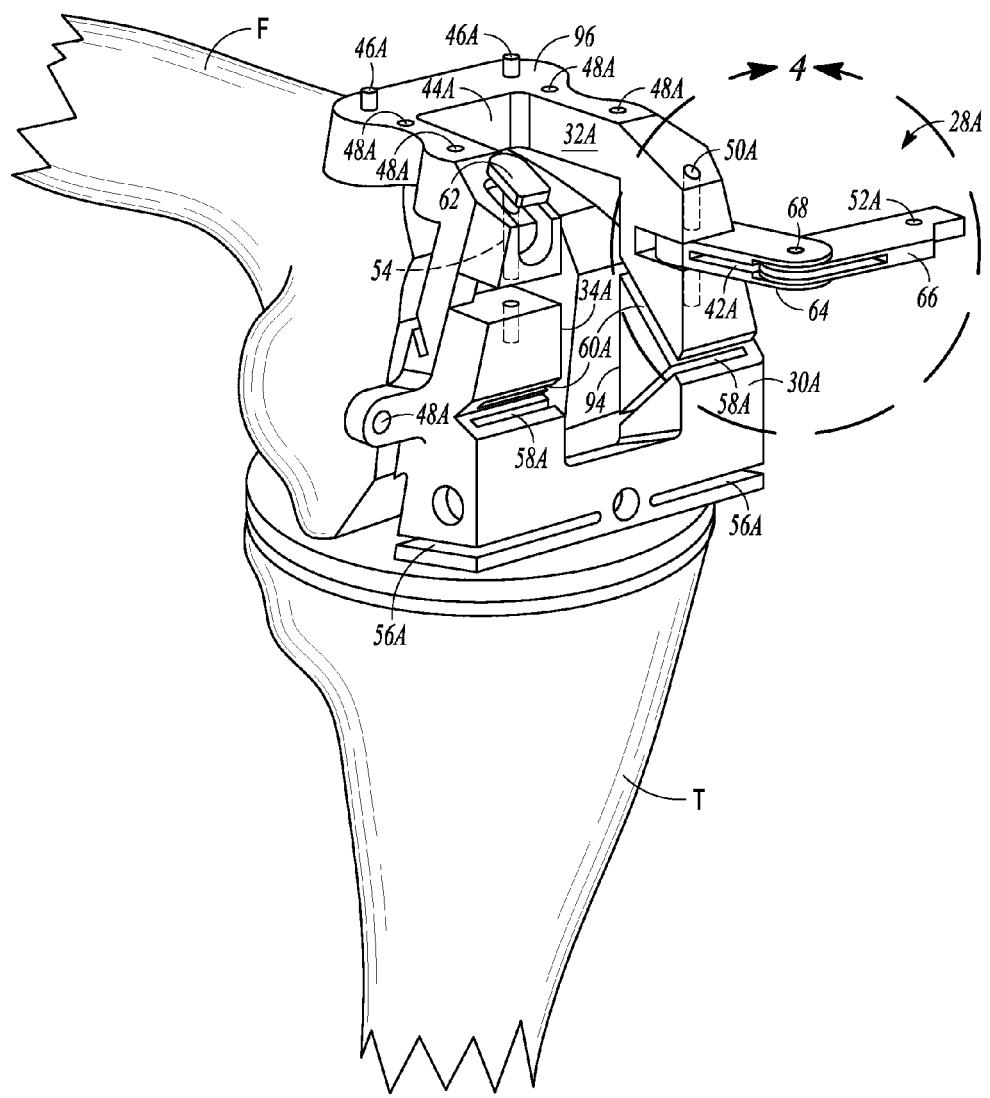
FIG. 3 is a perspective view of a knee joint with an alternative embodiment orthopedic guide assembly of the present disclosure incorporating a secondary guide body formed of a first secondary guide body arm rotatably connected to a second secondary guide body arm, with the secondary guide body rotated into a non-operative position.
Figure 4:
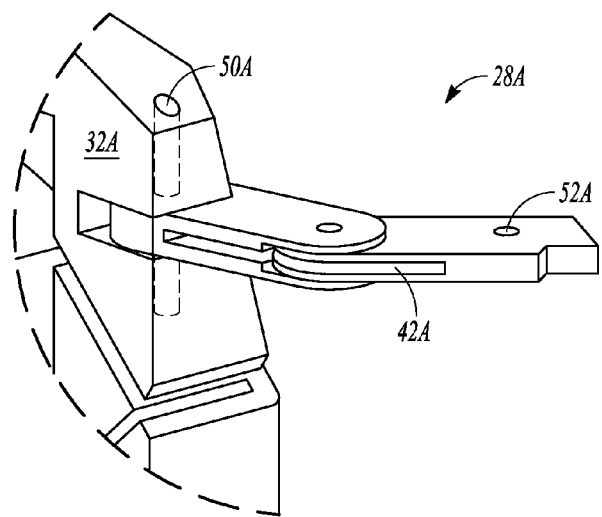
FIG. 4 is a segmented view of the orthopedic guide assembly illustrated in FIG. 3, showing the first and second secondary guide body arms aligned as they would be when the secondary guide body of this form of the present disclosure is placed in an operative position in which the secondary guide is operably positioned to guide preparation of an osteotomy of the femur.

FIGS. 3 and 4 illustrate alternative embodiment orthopedic guide assembly 10*a*. Orthopedic guide assembly 10*a* shares many similar parts to orthopedic guide assembly 10 illustrated in FIGS. 1 and 2. Such parts are indicated with similar reference numerals followed by an alphabetic designation. As illustrated in FIGS. 3 and 4, secondary guide body 28*a* includes first secondary guide body arm 64 and second secondary guide body arm 66. First secondary guide body arm 64 is pivotally connected to primary guide body 30*a* via pivot pin 50*a*. Similarly, second secondary guide body arm 66 is pivotally connected to first secondary guide body arm 64 via pivot pin 68. In this embodiment, secondary guide body 28 can be rotated about both pivot pin 50*a* and pivot pin 68 to position secondary guide body 28 in the non-operative position illustrated in FIG. 3. Each of first secondary guide body arm 64 and second secondary guide body arm 66 include cut slots 42*a*. Cut slots 42*a* are aligned as illustrated in FIG. 4 when secondary guide body 28*a* is positioned in an operable position similar to that depicted with respect to secondary guide body 28 in FIG. 2.

Figure 6:
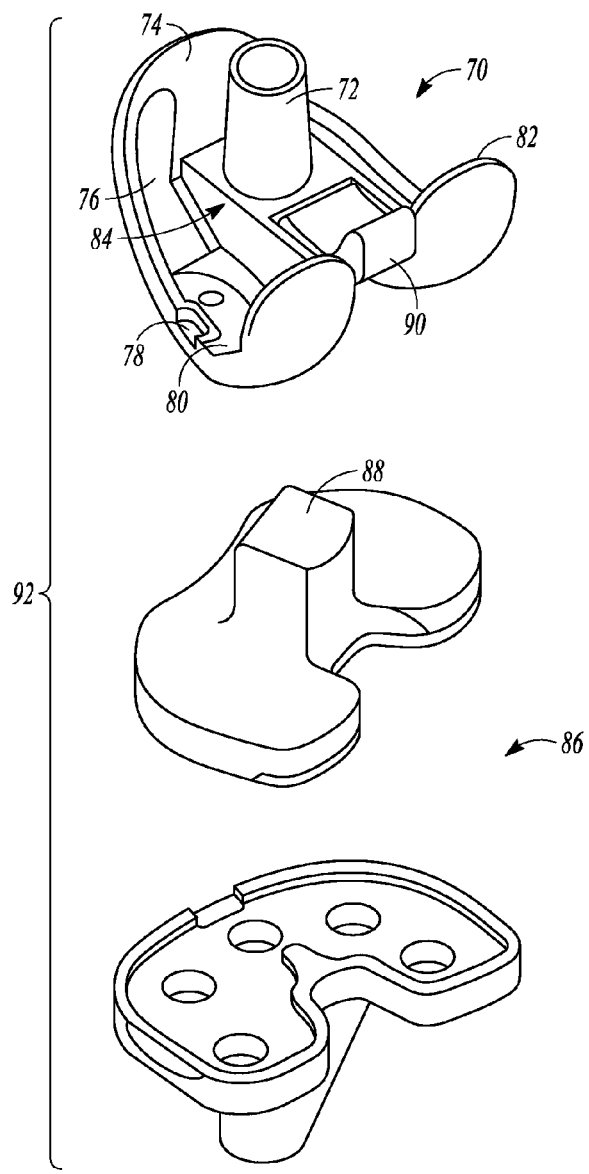
FIG. 6 is an exploded view of a posterior stabilized knee prosthesis.

As indicated above, the orthopedic guide assembly of the present disclosure can be utilized to prepare femur F as illustrated in FIG. 5. With this preparation, femoral component 70 (FIG. 6) can be secured to femur F. Prior to securement, a bore may optionally be formed through intercondylar box facet 24 to accommodate stem 72. Once this has been done, anterior bone contacting surface 74, anterior chamfer 76, distal bone contacting surface 78, posterior chamfer 80 and posterior bone contacting surface 82 of femoral component 70 can be brought into juxtaposition with anterior facet 12, anterior chamfer facet 14, distal facet 16, posterior chamfer facet 18 and posterior facet 20 of femur F, respectively, to allow for securement of femoral component 70 to femur F. Additionally, intercondylar box 84 can be positioned within the intercondylar box formed in femur F by intercondylar box facets 22, 24 and 26. With femoral component 70 of knee prosthesis 92 secured to femur F, tibial prosthesis 86 may be secured to tibia T to complete the prosthetic knee replacement. When fully assembled, knee prosthesis 92 will operate with spine 88 positioned within intercondylar box 84 such that cam 90 is brought into contact with the posterior surface of spine 88 during flexion of knee prosthesis 92.

While the present disclosure has been described as having exemplary designs, the present disclosure can be further modified within the spirit and scope of this disclosure. This application is therefore intended to cover any variations, uses or adaptations of the disclosure using its general principles. Further, this application is intended to cover such departures from the present disclosure as come within known or customary practice in the art to which this disclosure pertains.

What is claimed is:

1. An orthopedic guide assembly, comprising:
a primary guide body having a bone contacting surface and a primary guide body opposing surface opposite said bone contacting surface, said primary guide body defining a first primary guide surface extending between said bone contacting surface and said primary guide body opposing surface, said first primary guide surface sized and shaped to guide a primary osteotome to prepare a first primary osteotomy of a bone, said first primary guide surface having a first primary guide surface extent over which the primary osteotome can be guided to prepare a full extent of the primary osteotomy of the bone, said primary guide body having a distal femoral cut guide, the distal femoral cut guide defining a posterior guide surface sized and shaped to guide one of the primary osteotome and a secondary osteotome to prepare a posterior facet of a femur to receive a posterior bone contacting surface of a femoral prosthesis thereon, the distal femoral cut guide further defining a posterior chamfer guide surface sized and shaped to guide one of the primary osteotome and the secondary osteotome to prepare a posterior chamfer facet of the femur to receive a posterior chamfer bone contacting surface of the femoral prosthesis thereon, the distal femoral cut guide further defining an anterior chamfer guide surface sized and shaped to guide one of the primary osteotome and the secondary osteotome to prepare an anterior chamfer facet of the femur to receive an anterior chamfer bone contacting surface of the femoral prosthesis thereon said s posterior guide surface defining a posterior guide surface plane, said posterior chamfer guide surface defining a posterior chamfer guide surface plane, said anterior chamfer guide surface defining an anterior chamfer guide surface plane, said posterior guide surface plane intersecting said posterior chamfer guide surface plane and said anterior chamfer guide surface plane, said posterior chamfer guide surface plane intersecting said anterior chamfer guide surface plane; and a secondary guide body having a bone-side surface and a secondary guide body opposing surface opposite said bone-side surface, said secondary guide body defining a secondary guide surface extending between said bone-side surface and said secondary guide body opposing surface, said secondary guide surface sized and shaped to guide a selected one of the primary osteotome and the secondary osteotome to prepare a secondary osteotomy of the bone, said secondary guide body rotatably connected to said primary guide body, said secondary guide body rotatable from an operative position in which said secondary guide is operably positioned to guide preparation of the secondary osteotomy to a non-operative position in which said secondary guide is not capable of guiding preparation of the secondary osteotomy, in said operative position said secondary guide body presents a barrier to movement of the primary osteotome guided by said first primary guide surface so that movement of the primary osteotome is restricted to less than movement over a full extent of the first primary guide surface extent when said secondary guide body maintains said operative position, in said non-operative position said secondary guide body does not present the barrier to movement of the primary osteotome guided by said first primary guide surface to less than movement over the full extent of the first primary guide surface extent, said first primary guide surface extent fully accessible by the primary osteotome to prepare the full extent of the primary osteotomy of the bone when said secondary guide body maintains said non-operative position and said first primary guide surface extent is not fully accessible by the primary osteotome to prepare the full extent of the primary osteotomy of the bone when said secondary guide body maintains said operative position.

2. The orthopedic guide assembly of claim 1, wherein said first primary guide surface defines a planar first primary guide surface, said planar first primary guide surface defining a first primary guide surface plane, said secondary guide surface defining a secondary guide surface plane, said first primary guide surface plane forming an angle with said secondary guide surface plane when said secondary guide body maintains said operative position, said first primary guide surface plane further forming said angle with said secondary guide surface plane when said secondary guide body maintains said non-operative position.

3. The orthopedic guide assembly of claim 2, wherein said first primary guide surface plane is orthogonal to said secondary guide surface plane.

4. The orthopedic guide assembly of claim 1, wherein, in said operative position, said secondary guide surface is sized, shaped and positioned to guide one of the primary osteotome and the secondary osteotome to prepare an anterior facet of the femur to receive an anterior bone contacting surface of the femoral prosthesis thereon.

5. The orthopedic guide assembly of claim 1, wherein said primary guide body further defines a second primary guide surface extending between said bone contacting surface and said primary guide body opposing surface, said second primary guide surface sized and shaped to guide the primary osteotome to prepare a second primary osteotomy of the bone, said second primary guide surface facing said first primary guide surface, said first primary guide surface spaced a distance from said second primary guide surface so that said first primary osteotomy of the bone and said second primary osteotomy of the bone comprise opposing facets of an intercondylar box osteotomy.

6. The orthopedic guide assembly of claim 1, further comprising:
a retainer positioned to selectively retain said secondary guide body in said operative position.

7. The orthopedic guide assembly of claim 6, further comprising;
a second retainer positioned to selectively retain said secondary guide body in said operative position, whereby one of said retainer and said second retainer can selectively serve as a pivot rotatably connecting said secondary guide body to said primary guide body.

8. The orthopedic guide assembly of claim 1, wherein said secondary guide body comprises:
a first secondary guide body arm, said first secondary guide body arm rotatably connected to said primary guide body; and
a second secondary guide body arm, said second secondary guide body arm rotatably connected to said first secondary guide body arm, said secondary guide surface of said secondary guide body extending from said first secondary guide body arm to said second secondary guide body arm.

9. The orthopedic guide assembly of claim 1, wherein said posterior guide surface forms an angle of about 45 degrees with a distal portion of said bone contacting surface of said primary guide body.

10. An orthopedic instrument set, comprising:
a primary osteotome, comprising:
a primary osteotome blade; and
a primary osteotome handle extending from said primary osteotome blade;
a secondary osteotome, comprising:
a secondary osteotome blade; and
a secondary osteotome handle extending from said secondary osteotome blade;
a primary guide body having a bone contacting surface and a primary guide body opposing surface opposite said bone contacting surface, said primary guide body defining a first primary guide surface extending between said bone contacting surface and said primary guide body opposing surface, said first primary guide surface sized and shaped to guide said primary osteotome blade to prepare a first primary osteotomy of a bone, said first primary guide surface having a first primary guide surface extent over which said primary osteotome blade can be guided to prepare a full extent a primary osteotomy of the bone, said primary guide body having a distal femoral cut guide, the distal femoral cut guide defining a posterior guide surface sized and shaped to guide one of the primary osteotome and the secondary osteotome to prepare a posterior facet of a femur to receive a posterior bone contacting surface of a femoral prosthesis thereon, the distal femoral cut guide further defining a posterior chamfer guide surface sized and shaped to guide one of the primary osteotome and the secondary osteotome to prepare a posterior chamfer facet of the femur to receive a posterior chamfer bone contacting surface of the femoral prosthesis thereon, the distal femoral cut guide further defining an anterior chamfer guide surface sized and shaped to guide one of the primary osteotome and the secondary osteotome to prepare an anterior chamfer facet of the femur to receive an anterior chamfer bone contacting surface of the femoral prosthesis thereon, said posterior guide surface defining a posterior guide surface plane, said posterior chamfer guide surface defining a posterior chamfer guide surface plane, said anterior chamfer guide surface defining an anterior chamfer guide surface plane, said posterior guide surface plane intersecting said posterior chamfer guide surface plane and said anterior chamfer guide surface plane, said posterior chamfer guide surface plane intersecting said anterior chamfer guide surface plane;

a secondary guide body having a bone-side surface and a secondary guide body opposing surface opposite said bone-side surface, said secondary guide body defining a second primary guide surface extending between said bone-side surface and said secondary guide body opposing surface, said second primary guide surface sized and shaped to guide a selected one of the primary osteotome and the secondary osteotome to prepare a secondary osteotomy of the bone, said secondary guide body rotatably connected to said primary guide body, said secondary guide body rotatable from an operative position in which said secondary guide is operably positioned to guide preparation of the secondary osteotomy to a non-operative position in which said secondary guide is not capable of guiding preparation of the secondary osteotomy, in said operative position said secondary guide body presents a barrier to movement of said primary osteotome blade guided by said first primary guide surface so that movement of the primary osteotome is restricted to less than movement over a full extent of the first primary guide surface extent when said secondary guide body maintains said operative position, in said non-operative position said secondary guide body does not present the barrier to movement of said primary osteotome blade guided by said first primary guide surface to less than movement over the full extent of the first primary guide surface extent, said first primary guide surface extent fully accessible by said primary osteotome to prepare the full extent of the primary osteotomy of the bone when said secondary guide body maintains said non-operative position and said first primary guide surface extent is not fully accessible by said primary osteotome to prepare the full extent of the primary osteotomy of the bone when said secondary guide body maintains said operative position.

11. The orthopedic instrument set of claim 10, wherein said first primary guide surface defines a planar first primary guide surface, said planar first primary guide surface defining a first primary guide surface plane, said secondary guide surface defining a secondary guide surface plane, said first primary guide surface plane forming an angle with said secondary guide surface plane when said secondary guide body maintains said operative position, said first primary guide surface plane further forming said angle with said secondary guide surface plane when said secondary guide body maintains said non-operative position.

12. The orthopedic instrument set of claim 11, wherein said first primary guide surface plane is orthogonal to said secondary guide surface plane.

13. The orthopedic instrument set of claim 10, wherein said secondary guide body is rotatably connected to said primary guide body by a pivot pin.

14. The orthopedic instrument set of claim 13, wherein said pivot pin is positioned to selectively retain said secondary guide body in said operative position.

15. The orthopedic instrument set of claim 10, wherein said first primary guide surface includes a tertiary guide surface orthogonal to said secondary guide surface.

16. The orthopedic instrument set of claim 10, wherein said first primary guide surface and said second primary guide surface are configured to be opposing facets of an intercondylar box osteotomy.

* * * * *